United States Patent [19]

Rule et al.

[11] Patent Number: 4,814,545
[45] Date of Patent: Mar. 21, 1989

[54] PROCESS FOR REMOVING IMPURITIES FROM AN AROMATIC STREAM

[75] Inventors: Mark Rule; Gerald C. Tustin, both of Kingsport, Tenn.; Regina M. Moncier, Bristol, Va.; Joseph F. Jeter, Kingsport, Tenn.

[73] Assignee: Eastman Kodak Company, Rochester, N.Y.

[21] Appl. No.: 245,485

[22] Filed: Sep. 19, 1988

[51] Int. Cl.$^4$ ................................................. C07C 7/12
[52] U.S. Cl. ................................. 585/824; 585/828; 210/762; 210/763
[58] Field of Search ................ 585/828, 824; 210/762, 210/763

[56] References Cited

U.S. PATENT DOCUMENTS

| | | | |
|---|---|---|---|
| 3,306,945 | 2/1967 | Conviser | 585/824 |
| 3,394,200 | 7/1968 | Sargent | 585/824 |
| 3,700,744 | 10/1972 | Berger et al. | 585/828 |
| 3,875,081 | 4/1975 | Young | 502/79 |

Primary Examiner—Ivars Cintins
Assistant Examiner—Cynthia L. Nessler
Attorney, Agent, or Firm—Charles R. Martin; William P. Heath, Jr.

[57] ABSTRACT

A process comprising removing alkyl-substituted aromatic compounds, alkyl compounds, or cycloalkyl compounds from an aromatic stream containing these compounds by contacting the aromatic stream with molecular oxygen in the presence of a zeolite.

13 Claims, No Drawings

PROCESS FOR REMOVING IMPURITIES FROM AN AROMATIC STREAM

This invention relates to a process to selectively remove alkyl, cycloalkyl and alkyl-substituted aromatic compounds from an aromatic stream which contains these compounds as impurities.

Petroleum and chemical process streams which are mainly composed of aromatic compounds often contain a wide variety of other organic compounds which are impurities in the stream. Various techniques have been developed to selectively remove these impurities from such streams, including extraction, distillation, crystallization, and chromatographic adsorption. These techniques are suitable for removing large quantities of impurities but are generally not effective for removing small quantities of impurities, especially where the impurities have similar boiling points or co-crystallize with the aromatic compounds. Often these low levels of impurities do not materially affect the quality of the product; however, in some instances downstream processes cannot tolerate even trace quantities of these impurities. Examples of such instances include benzene in nitration grade toluene and thiophenes in platforming feedstock.

Due to the large number of different impurities that can be found in any particular aromatic stream and also due to the varying level of each impurity, it is important that a process to remove these impurities has the ability to remove substantially all of the impurities, irrespective of boiling point, melting point, or chemical structure.

We have now found that low levels of alkyl, cycloalkyl and alkyl-substituted aromatic compounds, which can be regarded as impurities, can be removed from an aromatic stream by contacting the stream with air and a zeolite catalyst at elevated temperatures. In this process the alkyl, cycloalkyl and alkyl-substituted aromatic compounds are oxidatively decomposed to $CO_2$, $CO$, and $H_2O$. The unsubstituted aromatic compounds which comprise the majority of the stream are not oxidized and remain unchanged.

By the term "aromatic stream" we mean a stream of various hydrocarbon compounds wherein a substantial portion of the hydrocarbon compounds are unsubstituted aromatic compounds. These streams are often associated with the distillation of petroleum but other streams not associated with the distillation of petroleum are also within the scope of the invention. Examples of unsubstituted aromatic compounds include benzene, naphthalene, biphenyl, diphenyl ether, and dibenzofuran. Preferred compounds are benzene, naphthalene, and biphenyl. An especially preferred compound is naphthalene, since even highly refined naphthalene contains a number of trace impurities that are difficult to remove by conventional techniques.

Alkyl-substituted aromatics which are oxidatively decomposed by this process are benzene, naphthalene, biphenyl and diphenyl ether substituted with alkyl groups. Although not bonded by any particular theory, we speculate that the alkyl substituent activates the molecule toward oxidative decomposition by providing a site for oxygen to become attached to the molecule. The oxygenated molecule is relatively non-volatile and even less oxidatively stable, and therefore remains on the catalyst until completely decomposed to $CO$, $CO_2$ and $H_2O$. Alkyl substituents which cause the aromatic impurities to be susceptible to oxidative decomposition are C-1 to C-20 hydrocarbons. Examples include methyl, ethyl, propyl, isopropyl, butyl, cyclohexyl, hexyl, heptyl, decyl and the like. Olefinic substituents such as ethenyl, propenyl, isopropenyl, and cyclohexenyl are also active substituents. Specific examples of alkyl-substituted aromatic impurities which can be oxidatively decomposed by this process include toluene, ethylbenzene, isopropylbenzene, isopropenyl benzene, xylene, mesitylene, durene, indane, methylnaphthalene, tetralin, methyl indene, ethylnaphthalene, methylbiphenyl, isopropylbiphenyl, styrene, phenylactylene, and dimethylnaphthalenes.

Alkyl and cycloalkyl compounds which can be oxidatively decomposed by this process can be broadly described as a C-1 to C-20 cyclic or acyclic nonaromatic hydrocarbon compound. The acyclic alkyl compound can be branched or unbranched and preferably contains 1 to 12 carbons. Examples include, methane, ethane, butane, isobutane, pentane, 2-methylpentane, 2,2-dimethylpropane, methyl cyclopentane, and the like. These impurities are often present in aromatic feedstocks at low levels due to incomplete extraction of aromatics from paraffinic reformate, partial or complete hydrogenation of aromatics in hydrodealkylation or hydrodesulfurization reactions, and from cross-contamination in storage tanks. Often these hydrocarbon impurities are difficult or impossible to remove from the aromatic product by conventional techniques due to the similarities in physical properties such as boiling point and melting point with the aromatic feedstock. Preferably the cyclic alkyl contains 5 to 20 carbon atoms. Examples include cyclohexane, cyclobutane, cyclopentane, methyl cyclopentane, decalin, methyldecalin, dicyclohexyl, methyl dicyclohexyl and dimethyldecalin.

Although any amount of impurities can be removed by this process, generally the amounts of impurities is less than 10 weight percent of the aromatic stream. A more preferred level of impurities is 1% or less, and an especially preferred level is 0.5% or less. Since this process will selectively remove substantially all alkyl, cycloalkyl and alkyl-substituted impurities from aromatic streams, the exact amount and type of impurities is not critical.

The zeolites that can be employed in this invention can be generally described as having a pore opening greater than about 6 Angstroms, such as faujasite zeolites. Small pore zeolites which cannot admit aromatic molecules have not been found to be effective. The silicon to aluminum ratio is not critical, and can vary from 1:1 to 100:1; however, the lower the ratio the greater the activity of the catalyst. A preferred silicon to aluminum ratio is less than 10:1, and an especially preferred ratio is less than 5:1. The preferred counterions contained by the zeolite are those selected from the group consisting of hydrogen, alkaline, alkaline earth, and rare earth elements, but other main group or transition element ions are not detrimental. In general, the smaller the cation, the greater the selectivity and activity of the catalyst. Surprisingly, a variety of oxidation metals on conventional supports such as alumina proved to be ineffective for this reaction. Examples of catalysts effective for this reaction include LiX, NaX, KX, CaX, NaY, KY, HY, HReY, Na-omega, Na-mordenite, H-ZSM-5, H-Silicalite, and KL. Especially preferred catalysts include NaY, HY, and HReY. The exact choice of catalyst will depend to some extent on the thermal and oxidative stability of the nuclear aromatic feedstock; however, selection of the optimum catalyst is straightforward and can be readily determined by one skilled in the art. A preferred catalyst for benzene purification is HReY, while a preferred catalyst for naphthalene purification is NaY.

The temperature which can be employed range from 150° C. to 500° C. Below about 150° C. the reaction rate becomes unacceptably slow; above about 500° C. unselective combustion becomes dominant. A preferred temperature range is 200°–450° C. The optimum reaction temperature depends on the exact catalyst utilized. In general decreasing the cation size reduces the optimum reaction temperature, while increasing the silicon to aluminum ration increases it. The type of feedstock does not appreciably affect the optimum reaction temperature, however, linear alkanes require somewhat higher reaction temperatures to combust than cycloaliphatic and alkylaromatic impurities. In general, however, the preferred catalysts can be operated over a broad temperature range.

The pressure which can be employed is not critical, and subatmospheric and superatmospheric pressures are suitable. A preferred pressure is from 0.2 to 20 atmospheres.

Any source of molecular oxygen is suitable with air being most preferred. Pure oxygen can also be used.

The aromatic stream and air are contacted in the presence of the zeolite by techniques well known in the art. For example, the liquid aromatic feed can be evaporated at elevated temperatures, mixed with air, and then contacted with the zeolite catalyst. Another method is to contact the zeolite catalyst directly with the liquid aromatic stream and an oxygen containing gas. Preferably, the aromatic stream is substantially in the vapor phase before contacting the zeolite catalyst.

Although this invention can be utilized to remove impurities from any aromatic stream, a particularly preferred embodiment is the selective removal of alkylaromatics from naphthalene. Naphthalene as obtained from coal tar and/or petroleum refining can contain a variety of alkyl-substituted aromatic species which cannot be conveniently removed by conventional methods, such as distillation and crystallization, due to their close boiling points and tendency to cocrystallize with naphthalene.

EXAMPLES 1–12

In the following examples the selective removal of an alkyl-substituted aromatic (toluene) from an aromatic stream composed of the alkyl-substituted aromatic and benzene is demonstrated. In all runs an 8.4 mole% solution of toluene in benzene was fed at a rate of 0.0304 mL/min over 10 cc of catalyst with 100 mL/min air. The furnace temperature was held at 300° C.; the reaction temperature is reported as the bed temperature. The % conversion column reports the percent of toluene removed from the product.

| Example | Catalyst | Bed Temp (C.°) | % Conversion |
|---|---|---|---|
| 1. | NaX | 350 | 88 |
| 2. | KX | 350 | 84 |
| 3. | NaY | 324 | 86 |
| 4. | HY | 356 | 94 |
| 5. | NaA | 302 | 5 |
| 6. | 13% $SiO_2Al_2O_3$ | 313 | 15 |
| 7. | CdY | 324 | 81 |
| 8. | $Al_2O_3$ | 300 | 0 |
| 9. | 5% Ni—$Al_2O_3$ | 300 | 0 |
| 10. | 5% Cu—$Al_2O_3$ | 301 | 0 |
| 11. | 5% Co—$Al_2O_3$ | 300 | 0 |
| 12. | 5% Cr—$Al_2O_3$ | 301 | 0 |

EXAMPLES 13–18

In the following examples, an aromatic stream composed of benzene containing 1.0 wt. % toluene was fed at 0.0304 mL/min with 100 mL/min air over 5 cc of the indicated catalysts. The furnace temperature, the bed temperature, the % conversion of toluene, and the off gas analysis are reported. Under these conditions, complete combustion of toluene and 0% combustion of benzene would result in 0.45% $CO + CO_2$ in the offgas.

| Example | Catalyst | Temperature °C. Bed | Temperature °C. Furnace | % Conversion Toluene | % $CO + CO_2$ |
|---|---|---|---|---|---|
| 13. | HReY | 197 | 199 | 75.7 | 0.06 |
| | " | 302 | 299 | 91.1 | 0.30 |
| | " | 356 | 349 | 86.1 | 0.83 |
| | " | 461 | 398 | 76.1 | 12.17 |
| 14. | Na—omega | 198 | 199 | 13.7 | — |
| | " | 250 | 250 | 14.9 | 0.06 |
| | " | 462 | 450 | 58.7 | 3.23 |
| 15. | KY | 196 | 199 | 0.0 | — |
| | " | 247 | 250 | 28.0 | — |
| | " | 299 | 300 | 38.0 | — |
| | " | 384 | 348 | 59.0 | 11.63 |
| | " | 462 | 399 | 83.0 | 18.65 |
| 16. | LZM-5 | 299 | 299 | 46.1 | — |
| | " | 351 | 349 | 63.5 | — |
| | " | 409 | 397 | 56.3 | 1.74 |
| 17. | NaX | 197 | 199 | 9.6 | — |
| | " | 251 | 250 | 48.0 | 0.20 |
| | " | 312 | 299 | 77.0 | 1.60 |
| | " | 423 | 349 | 86.0 | 14.69 |
| 18. | NaY | 200 | 200 | 0 | — |
| | " | 305 | 300 | 46.0 | — |
| | " | 356 | 350 | 71.0 | 1.01 |
| | " | 428 | 400 | 83.0 | 5.00 |

EXAMPLES 19–21

In these examples, an aromatic stream of 1.0 wt % hexane, 1.0 wt % toluene, and 98.0 wt % benzene was fed at 0.0304 mL/min over 5 cc of the indicated catalysts. Results are reported as before.

| Example | Catalyst | Temperature °C. Bed | Temperature °C. Furnace | % Conversion Toluene | % Conversion Hexane | % $CO + CO_2$ |
|---|---|---|---|---|---|---|
| 19. | HY | 192 | 196 | 22 | 93 | 0.07 |
| | " | 243 | 246 | 63 | 100 | 0.16 |
| | " | 295 | 296 | 80 | 100 | — |
| | " | 351 | 350 | 97 | 100 | 1.81 |
| 20. | CaX | 298 | 300 | 11 | 93 | 0.12 |
| | " | 363 | 350 | 85 | 100 | 1.23 |
| | 13% $SiO_2$—$Al_2O_3$ | 196 | 198 | 0 | 0 | — |

| Example | Catalyst | Temperature °C. Bed | Temperature °C. Furnace | % Conversion Toluene | % Conversion Hexane | % CO + CO$_2$ |
|---|---|---|---|---|---|---|
| 21. |  | 247 | 249 | 0 | 0 | — |
|  | " | 298 | 299 | 0 | 0 | — |
|  | " | 401 | 399 | 40 | 0 | — |

EXAMPLE 22

In this example, conditions were the same as in Example 18 except 15 cc of NaY were used and the furnace temperature was 350° C. The bed temperature was 361° C. and the toluene conversion was 96.3%, with 2.42% CO+CO$_2$ in the offgas.

EXAMPLE 23

In this Example 0.38 grams/min of an aromatic stream composed of naphthalene containing 0.05 wt % impurities, the major ones being tetralin and 2-methylnaphthalene, was fed with 135 mL/min air over 75 cc of NaX at a furnace temperature of 250° C. The bed temperature was 375° C., and the offgas contained 18% CO+CO$_2$. GC analysis of the product found 82% of the impurities had been removed.

EXAMPLE 24

In this example, 0.38 grams/min of an aromatic stream composed of naphthalene containing 0.08 wt % impurities, the major ones being tetralin and 2-methylnaphthalene, was fed with 135 ML/min. air over 100 cc of NaY at a furnace temperature of 275° C. The bed temperature was 281° C. and the offgas contained 0.3% CO+CO$_2$. GC analysis of the product found 96% removal of the impurities.

We claim:

1. A process for removing alkyl-substituted aromatic compounds, alkyl compounds, or cycloalkyl compounds from an aromatic stream containing these compounds comprising contacting the aromatic stream with molecular oxygen in the presence of a zeolite with a pore diameter greater than 6 Angstroms at a temperature in the range of 200° to 500° C.

2. The process of claim 1 wherein the alkyl portion of the alkyl-substituted aromatic compound contains 1 to 20 carbons.

3. The process of claim 2 wherein the alkyl-substituted aromatic compound is 2-methylnaphthalene.

4. The process of claim 2 wherein the alkyl-substituted aromatic compound is tetralin.

5. The process of claim 1 wherein the alkyl compound contains 1 to 20 carbons.

6. The process of claim 1 wherein the cycloalkyl compound contains 1 to 20 carbons.

7. The process of claim 6 wherein the cycloalkyl compound is decalin.

8. The process of claim 1 wherein the zeolite is a faujasite zeolite.

9. The process of claim 1 wherein the aromatic stream is a naphthalene containing stream.

10. The process of claim 1 wherein the aromatic stream is a benzene containing stream.

11. The process of claim 10 wherein the alkyl compound is methyl cyclopentane.

12. The process of claim 1 wherein the temperature is in the range of 200° to 450° C.

13. A process comprising removing tetralin and 2-methylnaphthalene from a naphthalene containing stream by contacting the naphthalene containing stream with molecular oxygen in the presence of a faujasite zeolite having a pore size greater than 6 Angstroms at a temperature in the range of 200° to 450° C.

* * * * *